United States Patent [19]

French

[11] Patent Number: 4,676,642
[45] Date of Patent: Jun. 30, 1987

[54] APPARATUS AND METHOD FOR REMOTE SENSING OF GASES, VAPORS OR AEROSOLS

[75] Inventor: Herbert A. French, Emsworth, United Kingdom

[73] Assignee: The Secretary of State for Defence in Her Britannic Majesty's Government of the United Kingdom of Great Britain and Northern Ireland, London, England

[21] Appl. No.: 708,790

[22] Filed: Mar. 6, 1985

[30] Foreign Application Priority Data

Mar. 14, 1984 [GB] United Kingdom ............... 8406690

[51] Int. Cl.$^4$ ........................... G01J 3/45; G01B 9/02
[52] U.S. Cl. .................................. 356/346; 356/353
[58] Field of Search ................... 356/346, 353, 35.5

[56] References Cited

U.S. PATENT DOCUMENTS

| | | | |
|---|---|---|---|
| 3,549,260 | 12/1970 | Barringer | 356/346 X |
| 3,563,663 | 2/1971 | Barringer | 356/346 |
| 3,914,055 | 10/1975 | Wolga et al. | 356/346 |
| 4,035,643 | 7/1977 | Barrett | 356/346 X |

OTHER PUBLICATIONS

"Digital Speckle-Pattern Shearing Interferometry", Nakadate et al., Applied Optics, 12-1980, pp. 4241-4246.

"Image-Shearing Camera for Direct Measurement of Surface Strains", Hung et al., Applied Optics, 4-1979, pp. 1046-1051.

"Simultaneous Measurement of Three Displacement Derivatives Using a Multiple Image-Shearing Interferometric Camera", Hung et al., Journal of Strain Analysis, 7-1979, pp. 81-88.

Primary Examiner—Davis L. Willis
Assistant Examiner—S. A. Turner
Attorney, Agent, or Firm—William R. Hinds

[57] ABSTRACT

A remote sensor for detecting gas, vapor or aerosol comprises means to measure the change in temporal coherence of light of a selected narrow waveband when it interacts with the gas etc. The light can be provided by a laser source or spectrally filtered sun light etc. Received radiation is split in to two beams by a Fresnel biprism and then detected by a detector sensitized by a modulating reticle to interference fringes. A glass delay plate of suitable thickness is placed in the path of one of the beams such that only received radiation having a temporal coherence greater than a minimum determined by the plate thickness produces an output signal from detector. The minimum temporal coherence is set higher than the temporal coherence of the illuminating radiation. In alternative arrangements a band-pass temporal coherence filter may be used and the sensor can be made to spectrally scan the field of view by using a tunable laser or a variable center frequency band-pass optical filter.

20 Claims, 12 Drawing Figures

APPARATUS AND METHOD FOR REMOTE SENSING OF GASES, VAPORS OR AEROSOLS

The invention relates to the detection of gases and vapours or aerosols by remote or semi-remote sensing and in particular to the measurement of changes in phase and amplitude occurring at the site of interaction between illuminating energy and the remote gas, vapour or aerosol.

Hereinafter the term gas is to be understood to include vapour or aerosol.

There are many requirements for the detection of gases by remote sensing. For example, the monitoring of pollution from ground stations by air-borne sensors and by satellites. The monitoring of some forms of pollution has been shown to be feasible from orbiting space craft, for example particulate pollution and smoke plumes have been observed.

Most of the techniques employed rely upon solar illumination for the remote sensing of gaseous pollutants and this is achieved by the identification of intensity changes in the spectrum characteristics of the reflected sunlight. Particularly severe problems have been encountered when using detection systems measuring in the ultraviolet (UV) since the solar energy at UV wavelengths is strongly absorbed by the ozonosphere, as for example in detecting pollution by sulphur dioxide. In the visible spectrum it has proved less difficult to design systems to detect for example oxides of nitrogen and halogens, while detection often becomes even easier in the infra-red region of the spectrum.

Before any particular remote sensing techniques can be chosen a fairly comprehensive understanding of the physics of the atmosphere and the special characteristics of the solar illumination at particular altitudes must be known. The sun provides a powerful wide-band source of illumination which is particularly convenient to use, however a limitation of daylight detection may not always be acceptable. Because of the effects of scattering and atmospheric absorption only a very weak background illumination is available at the earth's surface in the UV region of the spectrum. At wavelengths longer than the rear infra-red (at 3–5 $\mu$m) the thermal emissions from the earth's surface (taken as a 300k blackbody) are greater than the solar reflected energy, and the $CO_2$ absorption beyond the 12–14 micron waveband sets an upper limit to the practical use of the infra-red (IR) window.

The most widely used technique for remote detection is some form of correlation spectroscopy where a set of absorption bands is detected by one of the many basic types of spectrometer. The intensity profile of the dispersed spectrum is then modulated by a matching correlation mask, generally having alternate slits and bars, which is made to scan across the appropriate part of the optical spectrum. When the anticipated absorption spectrum is present in the received optical signal, a modulated signal of specific frequency content will appear at the output of a detector arranged behind the mask. This technique relies upon the detection of amplitude variation of the received spectrum, ie the change in absorption is detected by a change in signal amplitude (or intensity) against a background whose amplitude profile is a very complicated structure.

In the conventional amplitude sensitive system, by increasing the number of matching slits and bars in the correlation mask to a greater number of features on the absorption profile of the gas to be detected, a greaer degree of certainty-of-match can be obtained. However, as more spatial features are incorporated into the mask, more spatial harmonics are present with the consequence that other absorption spectra and irregularities in the background spectra may trigger a response.

The object of the present invention is to provide a sensor and method for remote detection of gases which is capable of high sensitivity and accuracy.

The invention comprises in one form a method for remote detection of a gas, vapour or aerosol comprising measurement of the change of temporal coherence of radiaion illuminating the gas, vapour or aerosol due to absorption of radiation thereby.

The temporal coherence of radiation of wavelength $\lambda$ is inversely proportional to the spectral line width $\delta\lambda$. The spectral bandwidth of the scattered energy after passage through the target gas becomes narrower when the bandwidth overlaps an absorption feature in the gas absorption spectrum and thus the effective temporal coherence of the radiation is increased. Then the greater the narrowing of the illuminating spectrum the greater the change in temporal coherence (or coherence length) and the better the instrumentation can sense the presence of the gas etc. To the extent that the spectrum of the illuminating radiation can be controlled then the target gas's absorption line may be altered in position relative to the illuminating spectrum. The optimum positions can be stated as occurring when the change of Fourier Transform of the illuminating spectrum due to the presence of the target gas is maximised. In a preferred active form of the method, radiation is transmitted and after reflection by the gas, vapour or aerosol is detected by a receiver co-located with the radiation transmitter.

Advantageously the receiver maybe arranged to discriminate against the transmitted radiation, responding only to radiation of longer temporal coherence than the transmitted radiation. In order to minimise false signals arising from any source of radiation of appropriately long temporal coherence (other than that returned from the target gas) which may be in the field of view the receiver may be arranged to respond only to increases in temporal coherence within a specified band-width. In an alternative semi-active arrangement use may be made of another illuminating source such as sunlight or other radiation not purposefully arranged as a transmitter. A broadband source like the sun can be appropriately band-limited at the receiver to imitate a narrow-band active source. In a final passive alternative the invention may be used to detect a target gas etc. which is self-illuminating. In the active, semi-active or passive arrangements provision may be made to spectrally scan the changes in temporal coherence or Fourier Transform.

The invention also provides apparatus for remote sensing of a gas, vapour or aerosol comprisingin one form: a transmitter capable of emitting radiation having a spectral line or band which at least partly overlaps a feature in the absorption spectrum of the gas, vapour or aerosol; radiation collecting means for receiving radiation from a predetermined field of view; and a detector responsive to changes in the temporal coherence of the transmitted radiation caused by interaction of the radiation with the gas, vapour or aerosol. Perferably the transmitter is a laser which may be tuned or the laser selected such that the transmitted radiation includes a spectral line or band in a wavelength range over which the target gas, vapour or aerosol has a changing absorption profile. In a second form suitable for semi-active or passive detection the transmitter may be replaced by a narrow-band transmission filter having a band-pass which at least partly overlaps a feature in the absorption spectrum of the gas, vapour or aerosol.

The receiver may include a high pass temporal coherence filter which is insensitive to the transmitted or illuminating radiation. Advantageously the temporal coherence filter includes an interferometer wherein received radiation is split into two beams and then recombined, one of the beams having a longer path length than the other. The interferometer can conveniently include a Fresnel biprism, and a glass delay plate may be placed in one of the beams. An amplitude modulating reticle may be placed in the path of the recombined beams and cyclically moved so as to sensitise the detector to interference fringes.

In an alternative arrangement the receiver may include a band pass temporal coherence filter with the lower band pass limit set above the temporal coherence of the transmitted or band-pass limited illuminating radiation. Conveniently the band pass temporal coherence filter may include a Michelson interferometer wherein the received radiation is split into two beams and then recombined with the path length of the beams being different, an optical delay being placed in a portion of one of the beams so as to increase the path length of the portion of the beam and detector means selectively responsive to interference fringes produced on recombination of one portion only of the one beam with the other beam. In one arrangement there may be provided a prism to separate the recombined beams to respective detectors for the selective response.

In the active form of the detector a turnable laser may be used together with means to scan the transmitted frequency such that the wavelength dependance of the change in Fourier Transform or temporal coherence can be determined.

In the semi-active or passive forms of the detector a tunable band-pass filter may be used to vary the passband of the received illumination, such that the wavelength dependence of the change in Fourier Transform or temporal coherence can again be determined.

The invention will now be described by way of example only with reference to the accompanying Drawings of which.

Figure 1:
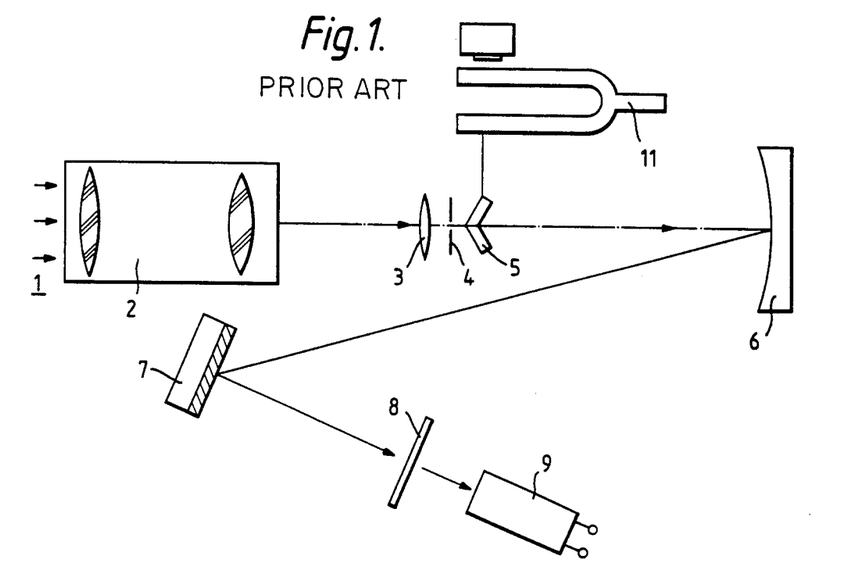
FIG. 1 illustrates a prior art correlation spectrometer.
Figure 2:
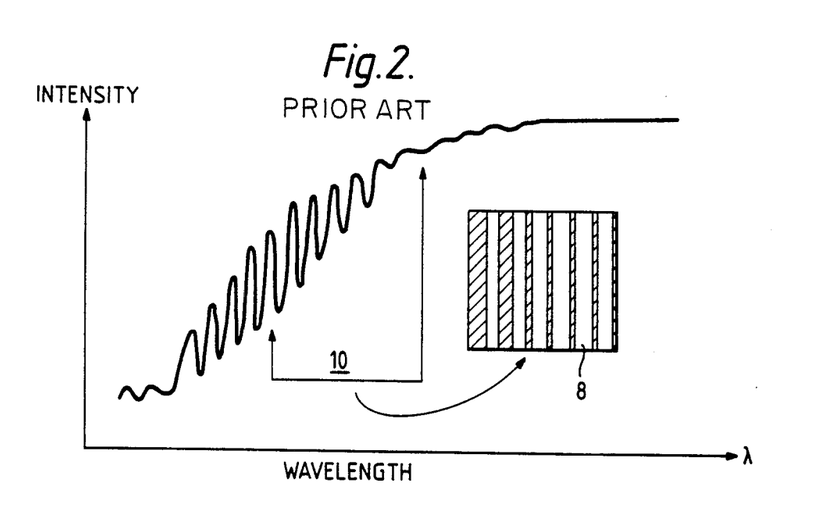
FIG. 2 shows the absorption spectrum of a target gas (sulphur dioxide) and the matching correlation mask used for its detection in the FIG. 1 arrangement.

FIGS. 1 and 2 illustrate the use of a conventional correlation spectrometer applied to the remote detection of gases. Light 1 from a target area is collected by an input lens system 2. The light is focussed by lens 3 on to an entrance slit 4 and then passes through a modulated refractor plate 5 to a concave mirror 6. Light from the concave mirror 6 is focussed on to a diffraction grating 7 and then passes through a correlation mask 8 to a photo-detector 9. FIG. 2 shows the absorption spectrum for sulphur dioxide in the wavelength region near 300 mm and this shows several sbsorption bands. The bands in the wavelength range 10 are matched to the alternating opaque and transparent strips on the correlation mask 8. As shown, when the correlation mask 8 is placed in register with the spectral range 10 the transmitted light will be a minimum. The action of the refractor plate 5, which is oscillated by an electronically maintained tuning fork 11, together with the lens 3 and entrance slit 4 arrangement, is to scan the spectral profile of the received light back-and-forth across the mask 8. When, as in this example, the received light has passed through a region of sulphur dioxide and absorption bands characteristic of sulphur dioxide are present in its spectrum then a modulated signal of specific frequency content will appear at the output of the detector 9. In this arrangement, as in other prior art arrangements, a change in absorption is detected by a change in signal amplitude (or intensity) against a background whose amplitude profile may be very complicated.

By increasing the number of matching slits and bars in the correlation mask 8 to a greater number of features on the absorption profile of the gas to be detected, a greater degree of certainty-of-match can be obtained. However, as more spatial features are incorporated into the mask, more spatial harmonics are present, with the consequence that other absorption spectra and irregularities in the background spectra may trigger a response and lead to a spurious signal.

The conventional correlation technique depends to a great extent on using compatible regions of the spectrum for both the target and the background. Firstly, adequate illumination must exist at a region which is suitable for a highly discriminating profile, and secondly the region must be reasonably clear from overlapping spectra having similar spatial frequencies. Solar illumination is advantageous because it is both broadband and intense. Lasers can provide a versatile source of illumination, however they have very narrow bandwidths and therefore the exploration of characteristics with wide spectral profiles, as in the correlation spectrometer described above, would be be extremely difficult and in most contexts impractical.

Figure 3A:
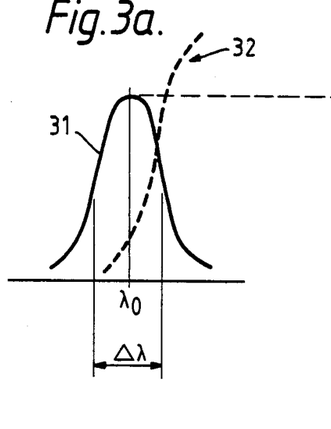
FIGS. 3a and 3b respectively show a typical spectrum of an illuminating narrow band-width source with a superimposed target gas absorption spectrum, and the spectrum of reflected and scattered radiation from the gas.
Figure 3B:
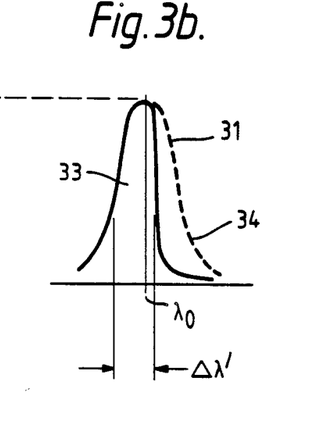

The present invention depends upon the changes in temporal coherence or the Fourier Transform which take place on interaction between the illuminating energy and the target gas in addition to other filtering processes. FIGS. 3a and 3b illustrate the basis for the technique. An illuminating source provides a narrow-band spectrum 31 (FIG. 3a) of nominal band width $\Delta\lambda$ and mean wavelength $\lambda_o$ Superimposed on this spectral profile is the absorption profile 32 of a gas to be detected. The spectral profile is shown overlapping the edge of the absorption spectral profile such that the absorption is wavelength dependent in the range $\Delta\lambda$. In the absence of the gas the profile 31 will be representative of that received by a remote detector as shown in FIG. 3b. With gas present, however, radiation transmitted through the gas (or reflected and scattered after passage through the gas) will have a spectral profile 33 of reduced band width $\Delta\lambda'$ at about the same mean wavelength $\lambda_o$, the shaded area 34 corresponding to the change in spectral profile.

The coherence length (Lc) of radiation of spectral width $\Delta\lambda$ is given by $$Lc = cTo = \frac{c}{\delta\lambda} = \frac{\lambda_o^2}{\delta\lambda}$$

where:
c = velocity of light;
$\lambda_o$ = mean wavelength of the radiation; and
$\delta\lambda$ = spectral width in wavelength units Hence, as the spectral bandwidth of the scattered energy after passage through the target gas becomes narrower, then the effective temporal coherence is increased. Thus the presence of scattered radiation at the appropriate nominal mean wavelength $\lambda_o$, equal to the transmitted wavelength but with increased temporal coherence, is an indication that the target gas is present at the remote site.

Figure 3C:
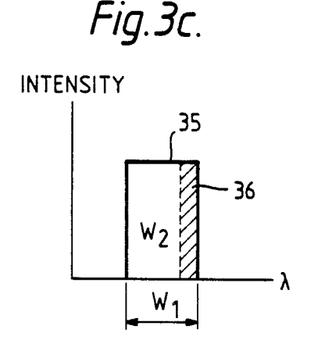
FIGS. 3c and 3d illustrate the dependence of the Fourier Transform change on the over lap of illuminating spectrum and target gas absorption spectrum.
Figure 3D:
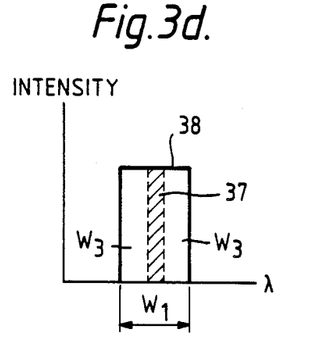

FIGS. 3c and 3d illustrate the dependence of the change of temporal coherence on the overlap of the illumination and absorption profiles. In both Figures the illumination and absorption spectra have sharp cut-offs and are rectangular in shape. FIG. 3c corresponds to FIGS. 3a and 3b, the change in coherence being brought about by the illuminating spectrum 35 being reduced in width from $W_1$ to $W_2$ by the absorption profile 36. In FIG. 3d the absorption profile 37 is in the centre of the illuminating spectrum 38. This leaves two lines of width $W_3$ ($=W_2/2$) with higher coherence.

Figure 3E:
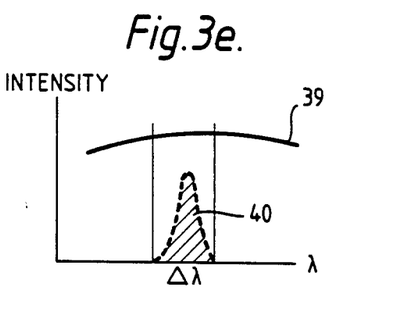
FIG. 3e illustrates the use of a band-pass filter to simulate the effects of FIGS. 3a–3d with broad-band illumination.

FIGS. 3a–3d illustrate narrow band illuminating sources and by contrast FIG. 3e illustrates how a broad-band source such as the sun may be used. The sun's spectrum 39 is band-pass limited to a narrow band which coincides with a target gas absorption profile 40 by providing a suitable filter at the receiver input.

FIG. 3e shows that broad band illumination, for example the solar spectrum 39, can be band-pass limited by an input filter of bandwidth $\Delta\lambda$ to achieve the same effects shown in FIGS. 3a to 3d by arranging the pass-band to coincide with the profile 40 of the target gas absorption spectrum.

Figure 4:
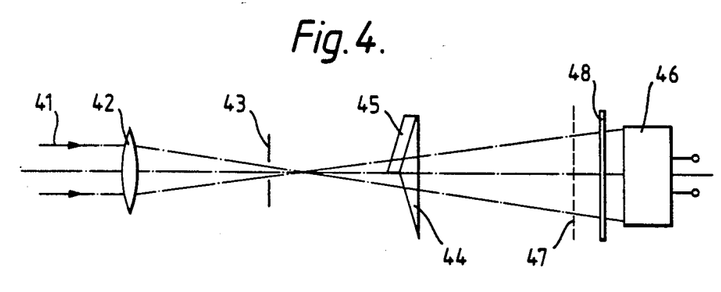
FIG. 4 shows a simple high-pass temporal coherence receiver employed by the invention.

A receiver capable of detecting temporal coherence changes for remote sensing should be selectively sensitive to small changes in temporal coherence and also should be insensitive to amplitude and intensity changes. FIG. 4 shows a simple version of a high pass temporal coherence optical receiver which may be used, according to the present invention, in the apparatus for remote detection of gases. Light 41 from a remote scene is transmitted via a lens 42 and a stop 43 to a Fresnel bi-prism beam splitter 44. One half-beam is delayed by a glass delay plate 45 and the combination of the two half-beams is measured by a detector 46. The glass delay plate 45 introduces an additional path length in the upper half-beam and thus interference fringes will be observed by the detector 46 if the path difference is smaller than the coherence length of the light 41. By approximate selection of the delay introduced by the delay plate 45 the receiver can be made to produce interference fringes only when the target gas is in the field of view. The detector is made selectively sensitive to the interference fringes of the appropriate wavelength by the modulating reticle 47 and the filter 48. The reticle is oscillated back and forth while the detector searches for a synchronous signal.

For the simple arrangement described above it is necessary to illuminate the volume of air to be searched by a source which can be tuned, or be arranged, to be adjacent to an appropriate absorption feature of the target gas or aerosol etc as shown in FIG. 3a. In many cases this can be achieved by current laser technology, and as more widely tunable lasers become available in the future, the difficulties of matching the illumination to the target's charcteristics can be expected to decrease. However, due to high sensitivity of the temporal coherence detection scheme, many more lasers are almost certainly suitable candidates as illuminators than would otherwise be available for the normal amplitude-sensitive electro-optical schemes. Due to the very narrow beam divergence and the near monochromatic nature of laser radiation, the power-spectral density at the target is high. Sources such the Xenon lamp, with its array of narrow spectral features, can have their broadband disadvantages offset to a great extent by the processing power of the temporal coherence detection system.

A spectrum scanning scheme may be employed by the use of an electronically tunable optical filter as are now becoming available. In this mode the narrow-band illuminating beam can be spectrally scanned across the absorption spectrum to yield a frequency-modulated signal, proportional to the temporal coherence variations caused by the convolution of the two spectra. As with the simple temporal coherence system, this scheme would be insensitive to amplitude variations as might be caused by for example: changes in transmitted power; variations in atmospheric turbulence and scatter; and changes in concentration of the target gas with position or air movement.

A periodic modulation at a separately arranged frequency can also be induced by means of a vibrating scanning prism or mirror so that the contours of the extent of the target can be mapped.

There are a number of distinct physical arrangements which can be used for remote sampling of a target gas 50. These are shown schematically in FIG. 5. A receiver 51, such as the one shown in FIG. 4, is colocated with an illuminating source 52 such as a laser. The receiver 51 can collect illumination scattered from the gas itself (indicated by 53) or scattered (54) from some remote surface 55 such as high ground or the side of a building etc. In some applications it may also be possible to employ a retro-reflector 56 to enhance the illumination (57) received by the detector system. The illumination 54, 57 reflected back towards the receiver from behind the target gas has made a double pass through the target gas and so provides an advantageous enhancement of the temporal coherence. The illuminating radiation may alternatively be received by a remote receiver 58 after direct-line transmission through the target gas or by a remote receiver 59 responsive to scattered light 60.

Figure 5:
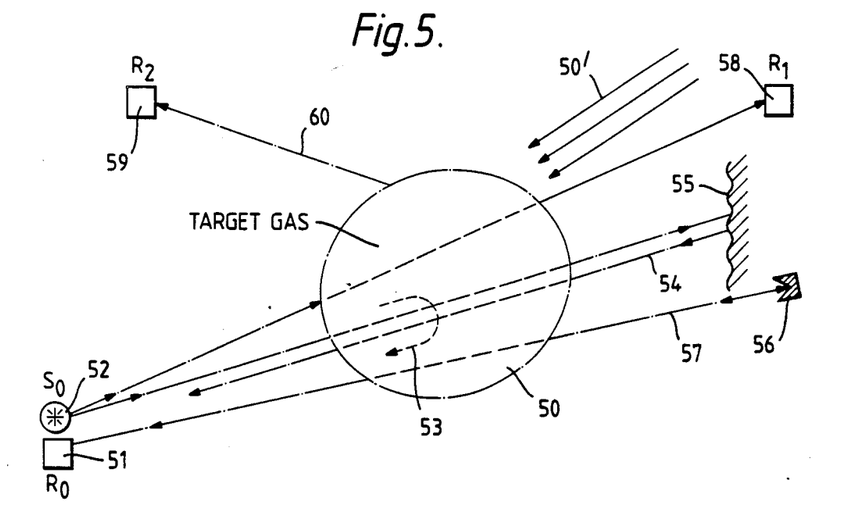
FIG. 5 shows schematically a number of remote gas detection arrangements.

In addition the receiver 51 may receive broad-band solar radiation 50' after transmission through the target gas.

The choice of detector system depends, among other factors, upon the absorption profile of the particular target gas and the spectrum and power of the source of illumination.

The power incident on the scattering surface is approximately:

$$W \exp(-\delta_a \cdot R) \cdot \exp(-\delta_g \cdot t)$$

where:
W is the illuminating power a collimated beam;
$\delta_a$ is the extinction coefficient of the normal air path;
$\delta_g$ is the extinction coefficient of the target gas cloud;
R is the range; and
t is the thickness of the cloud.

Assuming that the scattering surface has a reflectance value of r and is Lambertian, then the reflected power per unit solid angle is:

$$Wr \times \exp(-\delta_a \cdot R) \cdot \exp(-\delta_g \cdot t)$$

The power reaching the receiver is approximately given by:

$$W_{in} = Wr \times \exp(-2\delta_a \cdot R + \delta_g \cdot t)$$

Where the proportion of the reflected energy which passes back through the gas and enters the receiver is $Wr/W_{in}$.

The above expression gives only an approximate guide since it may be difficult to estimate values for $\delta_a$ and $\delta_g$, and the exact line profiles and their relative positions are important.

Figure 6:
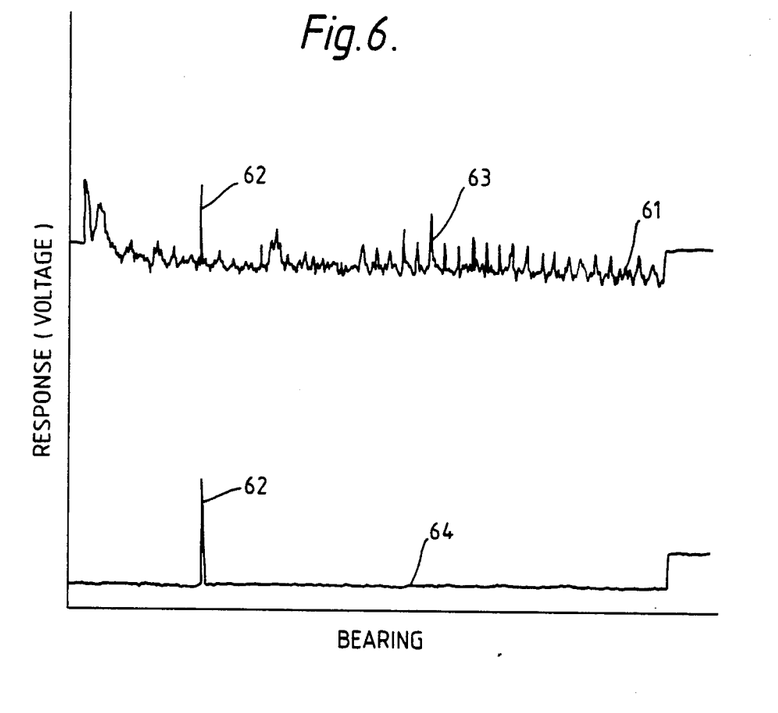
FIG. 6 shows the effect of temporal coherence filtering in an optical detection system.
Figure 7A:
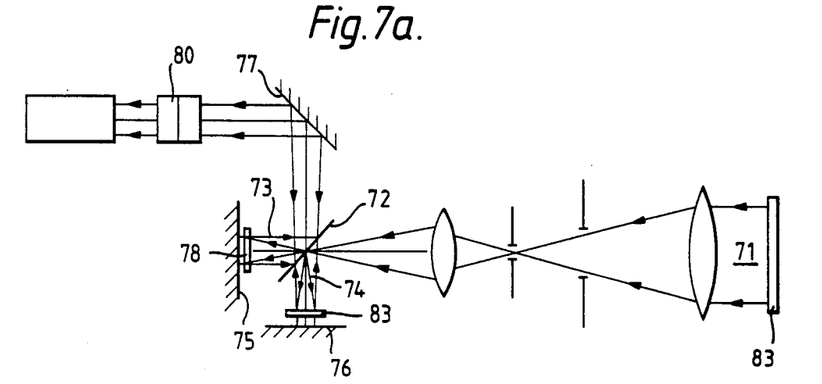
FIGS. 7a and 7b show a band pass temporal coherence sensor in plan and elevation.

The ability of the high pass temporal coherence receiver (FIG. 4) to eliminate background clutter is illustrated by the response curves in FIG. 6 obtained by scanning a field of view which includes a remote laser source. The upper trace shows the variation of response 61 against bearing measured by the FIG. 4 arrangement, but without the Fresnel biprism 44 and modulating reticle 47. The laser radiation 62 is indistinguishable from the background clutter 63 because the receiver responds only to intensity variations. The lower trace shows the effect of introducing the reticle 47 and fresnel biprism 44 with a thin glass plate delay 45 attached. Even a thin delay plate, discriminating against relatively short temporal coherence radiation, is found to reduce the background clutter (64) substantially and make the laser radiation readily detectable. When used in the remote gas sensor the thickness of the delay plate must then be increased until the laser light from the remote gas detector is just extinguished. Any increase in the temporal coherence of the laser radiation received after interaction with the target gas will then lead to interference fringes in the plane of the reticle 47 and the generation of a modulated signal at the output of the detector 46.

Where there is a light source in the field of view of narrower band-width than the illuminating source then the simple high pass from the beam splitter 72 compared with mirror 75. By arranging a near balance between the two delays introduced by the mirror offset and glass delay plate, very fine differences in temporal band-pass setting can be achieved. As can be seen particularly in FIG. 7b the positioning of the glass delay plate 78 leads to a beam 79 in which the upper half requires a lower temporal coherence in the incident light 71 for the presence of interference than the lower half. The two half beams are separated by the prism 80 and detected by separate detectors 81, 82. A phase modulator 83 comprising a glass delay plate which is tilted up and down cyclically produces periodic variations in intensity of any fringe patterns present at the detectors 81 and 82.

Figure 7B:
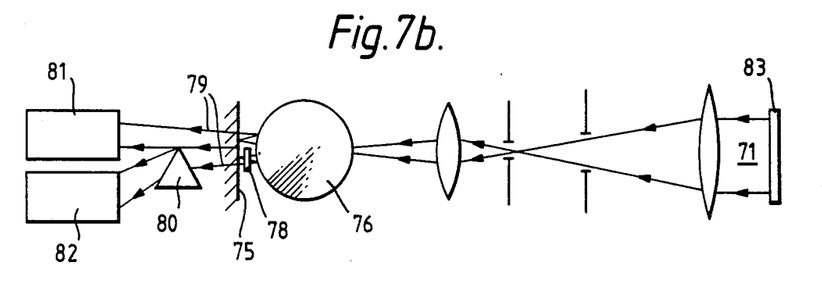

Thus in this arrangement the temporal coherence band pass is determined by varying the offset of the mirror 76 and the thickness of the glass delay plate 78.

By providing simple spectral band-limiting and electronic correlation the remote-sensing technique can be optimised.

The juxta position of the target gas's absorption line and illuminating spectrum might not be ideal in practice. Each case would need to be separately judged because the spectra would be different and technical limitations might prevent achievement of the most efficient illuminator. This problem may be eased by measuring $\partial(FT)/\partial\lambda$: the wavelength dependence on the Fourier Transform (or the temporal coherence). In the active detector, a turnable laser illuminator 52 may be frequency scanned. In a semi-active or passive detector making use of other sources illuminating a target gas or a self-illuminating target gas, the centre frequency of a turnable narrow bandpass filter 83 at the input to the receiver may be scanned. The scanning system would automatically reveal the maximum of the $\partial(FT)/\partial\lambda$ positions without the need for calculation and/or trial and error. In addition these systems would be more sensitive to gases whose absorption profiles were partially obscured by absorption in the intervening path (eg. atmospheric path).

The method of the invntion is also applicable when the area of interest is iluminated by sun's radiation, or when the area is illuminated by broad-band artificial sources such as arc lights, tungsten lamps, pyrotechnics, flares etc. A band-pass filter at the receiver input would be used to transmit an appropriate narrow spectral band unaffected by other sharp absorption spectra. Other modifications of the method and apparatus will be readily apparent to those skilled in the art, all falling within the scope of the invention described herein.

I claim:

1. A method for remote detection of a gas, vapour or aerosol comprising the following steps:
    (a) selection of a narrow spectral band-width of radiation, the said narrow band-width at least partly overlapping an absorption feature of the absorption spectrum of a gas to be detected;
    (b) determination of the temporal coherence length of said narrow band-width radiation in the absence of the gas to be detected;
    (c) measurement of the temporal coherence length of said narrow band-width of radiation received from a field of view; and
    (d) determination of the presence of the gas in said field of view from observation of whether the measured temporal coherence length of received radiation is greater than the determined temporal coherence length in the absence of the gas.

2. A method as claimed in claim 1 wherein radiation is transmitted and after reflection by the gas, vapour or aerosol is detected by a receiver co-located with the radiation transmitter.

3. A method as claimed in claim 1 wherein the illuminating radiation is sunlight and is band-pass filtered before it is detected by a receiver.

4. A method as claimed in claim 2 wherein the receiver is arranged to discriminate against the illuminating radiation, responding only to radiation of longer temporal coherence than the illuminating radiation.

5. A method as claimed in claim 4 wherein the receiver is arranged to respond only to increases in temporal coherence within a specified band-width.

6. A method as claimed in claim 5 wherein the change of temporal coherence of Fourier Transform is spectrally scanned.

7. A method as claimed in claim 6 wherein the radiation transmitter is scanned in frequency.

8. A method as claimed in claim 6 wherein the centre frequency of said specified band-width is scanned.

9. Apparatus for remote sensing of a gas, vapour or aerosol comprising:
   (a) a radiation transmitter capable of emitting radiation having a spectral line or band which at least partly overlaps an absorption feature in the absorption spectrum of the gas, vapour or aerosol;
   (b) radiation collecting means for receiving radiaion from a pre-determined field of view; and
   (c) a detector responsive to an increase in the temporal coherence length of a narrow spectral band of the radiation received caused by interaction of the transmitted radiation with the gas, vapour or aerosol.

10. Apparatus for remote sensing of a gas, vapour of aerosol comprising:
    (a) an input filter having a narrow spectral bandwidth which at least partly overlaps an absorption feature in the absorption spectrum of the gas, vapour or aerosol;
    (b) radiation collecting means for receiving radiation from a pre-determined field of view; and
    (c) a detector responsive to an increase in the temporal coherence length of the radiation received caused by interaction of the transmitted radiation with the gas, vapour or aerosol.

11. Apparatus as claimed in claim 9 wherein the receive includes a high pass temporal coherence filter which is insensitive to the transmitted or illuminating radiation.

12. Apparatus as claimed in claim 11 wherein the temporal coherence filter includes an interferometer wherein received radiation is split into two beams and then recombined, one of the beams having a longer path length than the other.

13. Apparatus as claimed in claim 12 wherein the interferometer includes a Fresnel biprism and a glass delay plate placed in the path of one of the beams.

14. Apparatus as claimed in claim 12 wherein an amplitude modulating reticle is placed in the path of the recombined beams and cyclically moved so as to sensitise the detector to interference fringes.

15. Apparatus as claimed in claim 9 wherein the receiver includes a band pass temporal coherence filter with the lower band pass limit set above the temporal coherence of the transmitted or band-pass limited illuminating radiation.

16. Apparatus as claimed in claim 15 wherein the band pass temporal coherence filter includes a Michelson interferometer wherein the received radiation is split into a first beam and a second beam and then recombined with the path length of said first and second beams being different, an optical delay being placed in a portion of the first one of the beams so as to increase the path length of said portion of the first beam and detector means selectively responsive to interference fringes produced on recombination of said portion only of the first beam with the second beam.

17. Apparatus as claimed in claim 16 wherein there is provided a prism to separate the recombined beams to respective detectors for the selective response.

18. A method as claimed in claim 3 wherein the receiver is arranged to discriminate against the illuminating radiation, responding only to radiation of longer temporal coherence than the illuminating radiation.

19. Apparatus as claimed in claim 10 wherein the receiver includes a high pass temporal coherence filter which is insensitive to the transmitted or illuminating radiation.

20. Apparatus as claimed in claim 10 wherein the receiver includes a band pass temporal coherence filter with the lower band pass limit set above the temporal coherence of the transmitted or band-pass limited illuminating radiation.

* * * * *